US00PP32581P2

(12) United States Plant Patent
de Ruyver

(10) Patent No.: US PP32,581 P2
(45) Date of Patent: Dec. 8, 2020

(54) ***LEPTOSPERMUM* PLANT NAMED 'RUYLEPLAR'**

(50) Latin Name: *Leptospermum scoparium*
Varietal Denomination: RUYLEPLAR

(71) Applicant: Kurt de Ruyver, Oudenaarde (BE)

(72) Inventor: Kurt de Ruyver, Oudenaarde (BE)

( * ) Notice: Subject to any disclaimer, the term of this patent is extended or adjusted under 35 U.S.C. 154(b) by 0 days.

(21) Appl. No.: 16/873,563

(22) Filed: May 6, 2020

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Samuel R. McCoy, Jr.

(57) ABSTRACT

A new and distinct variety of *Leptospermum* plant named 'RUYLEPLAR' which is characterized by the combination of a conical growth habit, an abundance of red-purple foliage on dark red stems, excellent heat and drought tolerance, and the stability of all characteristics from generation to generation.

2 Drawing Sheets

Latin name of the genus and species: The Latin name of the genus and species of the novel variety disclosed herein is *Leptospermum scoparium.*

Variety denomination: The inventive variety of *Leptospermum* disclosed herein has been given the variety denomination 'RUYLEPLAR'.

BACKGROUND OF THE INVENTION

Parentage: 'RUYLEPLAR' is a seedling selection which resulted from the controlled pollination of an unnamed *Leptospermum scoparium* plant with an upright growth habit (not patented), the seed parent, with *Leptospermum scoparium* 'Nanum' (not patented), the pollen parent. The crossing was made at a commercial nursery in Oudenaarde, Belgium, in March of 2017 and yielded 120 seedlings. The seedlings were grown to maturity in order to observe for unique growth characteristics. From these seedlings, 15 candidate plants were selected for further observation. In May of 2018, one of these 15 candidate plants was observed to exhibit a naturally conical growth habit with unique foliage. The plant was given the name, 'RUYLEPLAR'.

Asexual Reproduction: Asexual reproduction of 'RUYLEPLAR', by way of stem cuttings, was first initiated in January of 2020 at a commercial greenhouse in Heythuysen, the Netherlands. Through one subsequent generation, the unique features of this cultivar have proven to be stable and true to type.

SUMMARY OF THE INVENTION

The cultivar 'RUYLEPLAR' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'RUYLEPLAR'. These characteristics in combination distinguish 'RUYLEPLAR' as a new and distinct *Leptospermum* cultivar:

1. *Leptospermum* 'RUYLEPLAR' exhibits a naturally conical growth habit with a pyramidal profile; and
2. *Leptospermum* 'RUYLEPLAR' exhibits relatively small, finely textured foliage; and
3. *Leptospermum* 'RUYLEPLAR' exhibits an abundance of dark red-purple foliage borne on dark red stems; and
4. *Leptospermum* 'RUYLEPLAR' excellent drought and heat tolerance.

BOTANICAL DESCRIPTION OF THE PLANT

Figure 1:
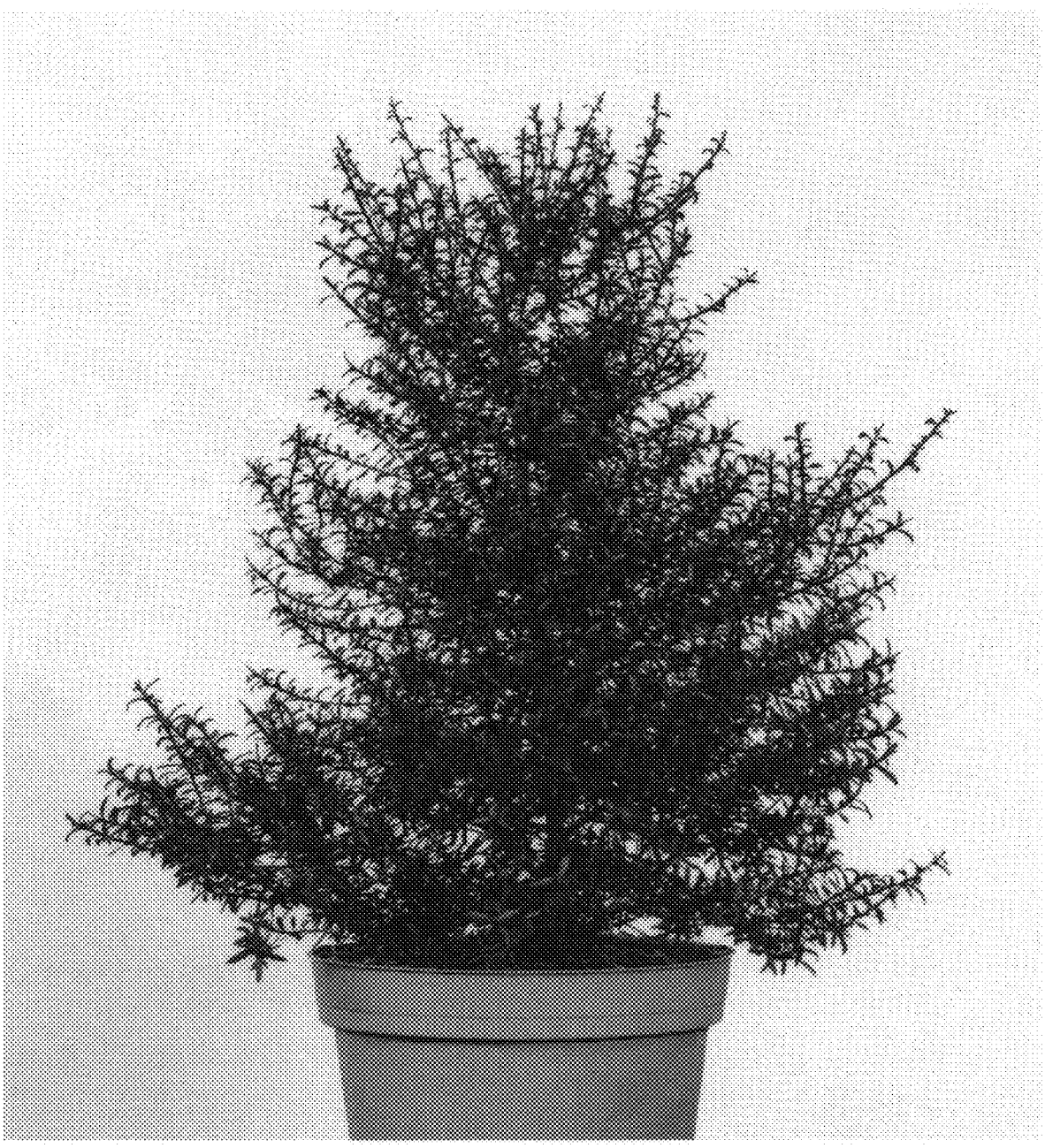
FIG. 1 illustrates, as nearly true as it is reasonably possible to make the same in color photographs of this type, an exemplary plant of 'RUYLEPLAR'. This plant is approximately 12 months old, shown planted in a 10.5 cm container.
Figure 2:
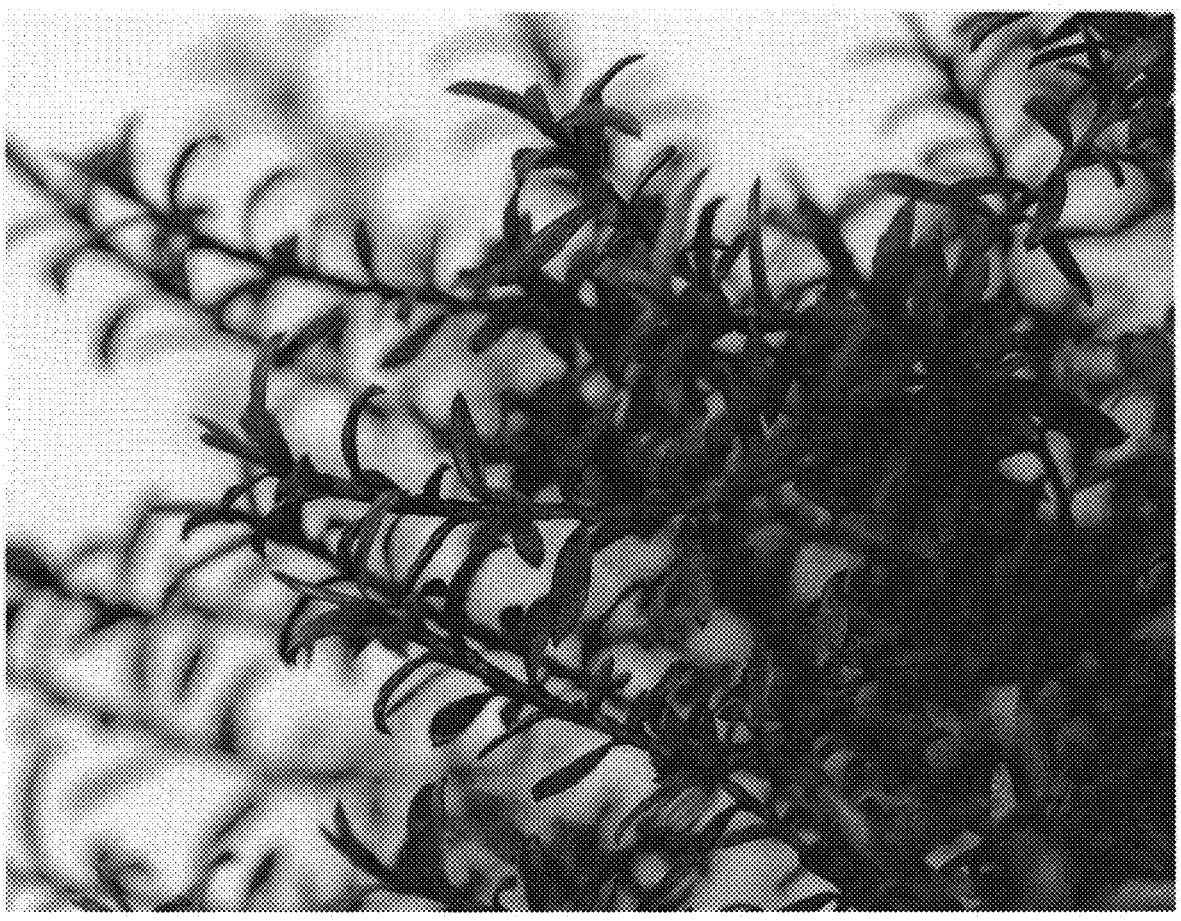
FIG. 2 illustrates, as nearly true as it is reasonably possible to make the same in color photographs of this type, the typical coloration of the foliage of 'RUYLEPLAR'.

The following observations and measurements were made in October of 2019 and describe a sample set of six 12 month-old 'RUYLEPLAR' plants grown in 10.5 cm nursery pots at a plant nursery in Heythuysen, the Netherlands. Plants were produced in an unheated greenhouse with full sun exposure, using conventional production protocols for *Leptospermum* which included infrequent irrigation and fertilizer applications using fertigation techniques. No pest or disease control measures were utilized in production.

Those skilled in the art will appreciate that certain characteristics will vary with older or, conversely, with younger plants. 'RUYLEPLAR' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'RUYLEPLAR' and comparisons with the parent plants are provided below.

Plant description:

*Growth habit*.—Conical growth habit.

*Plant profile*.—Pyramidal.

*Average height*.—21.8 cm from the soil level to the top of the foliar plane.

*Plant spread*.—Average of 22.5 cm.

*Growth rate*.—Moderately fast.

*Plant vigor*.—Moderately to highly vigorous.

*Propagation type*.—Stem cuttings.

*Time to produce a rooted cutting*.—Approximately 20 days to produce a rooted cutting at approximately 18 degrees Celsius.

*Time to produce a finished plant*.—20 weeks to produce a fully rotted 9 cm container.

*Disease resistance*.—Neither resistance nor susceptibility to typical *Leptospermum* pests and diseases has been observed.

*Environmental tolerances*.—Adapt to, at least, USDA Zones 9 through 12 and temperatures as high as 40 degrees Celsius; moderate tolerance to rain; moderate to high tolerance to wind.

Root system:

*General*.—Dense and very freely branched rooting; roots are moderately fibrous.

*Distribution in the soil profile*.—Shallow to moderately deep.

*Diameter of roots*.—0.1 cm on average.

*Texture*.—Smooth; no root hairs.

*Color*.—White, nearest to RHS N155C.

Stem:

*General branching habit*.—A single main stem, freely branching with lateral branches. Pinching isn't required but will improve branching.

*Quantity of main stems per plant*.—1.

*Quantity of lateral branches*.—33.

*Length of lateral branches*.—Approximately 11.1 cm.

*Diameter of lateral branches*.—Approximately 0.175 cm.

*Internode length*.—Approximately 0.2 cm.

*Attitude of lateral branches*.—At an average angle of 45 degrees to the main stem.

*Aspect*.—Rounded.

*Texture*.—Smooth, glabrous.

*Luster*.—Juvenile stems are moderately glossy; mature stems and oldest wood is matte.

*Strength*.—Strong.

*Color, juvenile*.—Greyed-purple, nearest to RHS 187A.

*Color, mature*.—Greyed-orange, nearest to RHS 166C.

*Color at internodes*.—Greyed-orange, nearest to RHS 166C.

*Color of the oldest wood*.—Greyed-brown, nearest to a mixture of RHS 199D and N199B.

Foliage:

*Arrangement*.—Alternate.

*Division*.—Simple.

*Quantity*.—Approximately 600 leaves per lateral branch.

*Attitude*.—At an average angle of 80 degrees to the branch.

*Fragrance*.—Pleasant sweet fragrance when crushed.

*Lamina*.—Shape — Narrow elliptic to narrow oblong. Aspect — Flat to very slightly carinate. Dimensions — 0.65 cm long and 0.15 cm wide. Apex — Acute. Base — Attenuate. Margin — Entire; not undulated. Texture of top surface — Smooth, glabrous, and very slightly glossy. Texture of bottom surface — Smooth, glabrous, and matte. Color — Juvenile foliage, adaxial surface — Nearest to in between greyed-purple and brown, RHS N186C and 200A; lightly suffused with yellow-green, nearest to RHS 147A. Juvenile foliage, abaxial surface — Greyed-purple, nearest to RHS 183B. Mature foliage, adaxial surface — Green, nearest to RHS NN137A. Mature foliage, abaxial surface — Green, nearest to RHS 137D. Venation — Pattern — Pinnate. Color, adaxial surface — Same as the surrounding foliage; green, nearest to RHS NN137A. Color, adaxial surface — Only the midrib is visible; green, nearest to RHS 137B.

*Petiole*.—Length — 0.5 cm. Diameter — 0.5 cm. Strength — Strong. Texture — Smooth; glabrous. Luster — Slightly glossy. Color, adaxial surface — Green, nearest to RHS 138A, and moderately suffused with greyed-red, nearest to RHS 182A. Color, abaxial surface — Green, nearest to RHS 138A, and moderately suffused with greyed-red, nearest to RHS 182A.

Inflorescence: No flowering has been observed to date.

COMPARISON WITH THE PARENT PLANT

Plants of the new cultivar 'RUYLEPLAR' differ from the seed parent, an unnamed *Leptospermum scoparium* plant with an upright growth habit (not patented), in the following characteristics described in Table 1 below.

TABLE 1

| Characteristic | 'RUYLEPLAR' | The seed parent. |
|---|---|---|
| Growth habit. | Conical. | Upright. |
| Overall plant height. | Shorter than the seed parent. | Taller than 'RUYLEPLAR'. |
| Foliage size. | Smaller than the seed parent. | Larger than 'RUYLEPLAR'. |
| General coloration of the foliage. | More towards dark red-purple. | More towards green. |

COMPARISON WITH THE CLOSEST KNOWN COMPARATOR

Plants of the new cultivar 'RUYLEPLAR' differs from the pollen parent and most similar commercial cultivar known to the inventor, *Leptospermum* 'Nanum' (not patented), in the following characteristics described in Table 2 below.

TABLE 2

| Characteristic | 'RUYLEPLAR' | 'Nanum' |
|---|---|---|
| Growth habit. | Conical. | Irregular globular. |
| Foliage size. | Smaller than 'Nanum'. | Larger than 'RUYLEPLAR'. |
| General coloration of the juvenile foliage. | More greyed-purple. | More towards green. |

That which is claimed is:

1. A new and distinct variety of *Leptospermum* plant named 'RUYLEPLAR', substantially as described and illustrated herein.

* * * * *